(12) United States Patent
Ravizza

(10) Patent No.: US 6,575,954 B1
(45) Date of Patent: Jun. 10, 2003

(54) DISPOSABLE SET PACKAGE FOR INFUSING A MEDICINAL FLUID INTO A PATIENT'S BODY

(75) Inventor: Renato Ravizza, Verona (IT)

(73) Assignee: Haemotronic Advanced Medical Technologies S.p.A. (IT)

( * ) Notice: Subject to any disclaimer, the term of this patent is extended or adjusted under 35 U.S.C. 154(b) by 0 days.

(21) Appl. No.: 09/518,061

(22) Filed: Mar. 2, 2000

(51) Int. Cl.7 ............................................. A61B 19/00
(52) U.S. Cl. ...................... 604/409; 604/408; 604/410; 604/246; 206/216; 206/363; 206/365; 206/366
(58) Field of Search ................. 604/171, 246, 604/161, 262, 255, 257, 251, 408, 410, 409, 6.15; 206/363–366, 216

(56) References Cited

U.S. PATENT DOCUMENTS

| | | | | |
|---|---|---|---|---|
| 3,006,341 A | * | 10/1961 | Poitras | |
| 3,311,268 A | * | 3/1967 | Fields | 222/159 |
| 4,432,763 A | * | 2/1984 | Manschot et al. | 604/262 |
| 4,867,743 A | * | 9/1989 | Vaillancourt | 604/135 |
| 4,968,301 A | * | 11/1990 | di Palma et al. | 604/246 |
| 5,354,281 A | * | 10/1994 | Chen | 604/177 |
| 5,389,384 A | * | 2/1995 | Jooste | 424/661 |
| 5,820,582 A | * | 10/1998 | Keilman | 604/49 |
| 5,843,049 A | * | 12/1998 | Heilmann et al. | 604/275 |
| 5,888,408 A | * | 3/1999 | Nagels | 210/789 |

* cited by examiner

Primary Examiner—Ira S. Lazarus
Assistant Examiner—Tu Cam Nguyen
(74) Attorney, Agent, or Firm—Alan H. Gordon & Associates

(57) ABSTRACT

The disposable set includes an infusion device having an outflow conduit and a needle. The packager is defined by a single bag made of transparent, flexible, plastic material and having a first compartment enclosing the medicinal fluid, and a second compartment enclosing the infusion device. The two compartments are formed from two sheets of the aforementioned material, heat sealed along the outer edges of the sheets, so as to be sealed with respect to the outside environment, and the compartments are also separated in airtight manner from each other by another seal. The conduit communicates with the first compartment via a chamber formed by a further seal and acting as a drip for visually controlling the infusion treatment.

7 Claims, 1 Drawing Sheet

DISPOSABLE SET PACKAGE FOR INFUSING A MEDICINAL FLUID INTO A PATIENT'S BODY

The present invention relates to a disposable set package for infusing a medicinal fluid into a patient's body.

BACKGROUND OF THE INVENTION

Medicinal infusions, as in dialysis treatment for example, require a container for the fluid, and an infusion device comprising an infusion needle and at least one outflow conduit connecting the needle to the container. All these components, commonly referred to as a "set", are normally supplied in separate packages, or in a single package, but as separate components which must be assembled and sterilized prior to use.

To reduce the risk of contagion and the cost of washing the components, the recent trend has been to use all the components only once, including the infusion needle. Nevertheless, assembling the components prior to use involves extremely careful handling and possibly also sterilization of the handled components.

Document EP-A-136 775 describes a package for administering fluid to a patient nasally, and wherein a sheet of semirigid plastic is folded into three, and the respective edges sealed to form a compartment for the fluid and a compartment for a medical device defined by a conduit and a nasal infuser. On account of the semirigid sheet to be folded into three, the above package is fairly complicated to produce, is extremely bulky, and is unsuitable for use with a fluid and a needle infusion device.

SUMMARY OF THE INVENTION

It is an object of the present invention to provide a disposable set package for infusing a medicinal fluid using a needle, which is extremely straightforward and designed to eliminate the aforementioned drawbacks typically associated with known technology. It is a further object of the invention to provide the disposable set with a transparent drip enabling visual control of the infusion treatment.

According to the present invention, there is provided a disposable set package comprising an infusion device having an outflow conduit connected to a needle, and characterized in that said package is defined by a single bag made of flexible plastic material and comprising a first compartment enclosing said fluid, and a second compartment enclosing said infusion device; said conduit communicating with said first compartment; and said two compartments being sealed with respect to the outside environment.

According to a further aspect of the invention, the plastic material of the bag is transparent, the two compartments are separated by a seal in the bag, and the package has a further seal forming, between said conduit and said first compartment, a transparent chamber acting as a drip.

BRIEF DESCRIPTION OF THE DRAWINGS

A preferred, non-limiting embodiment of the invention will be described by way of example with reference to the accompanying drawings, in which.

DETAILED DESCRIPTION OF THE INVENTION

Figure 1:
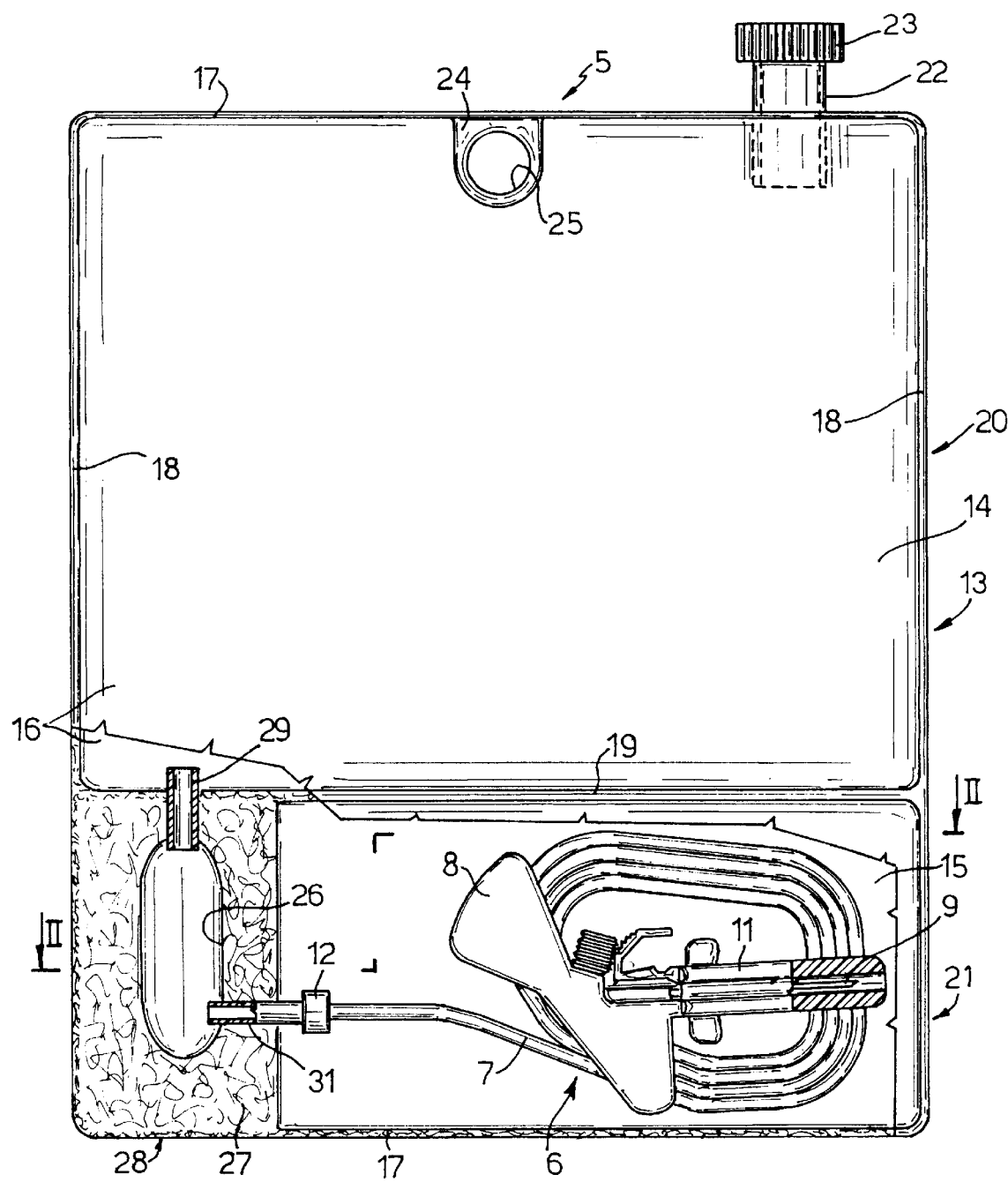
FIG. 1 shows a partially sectioned front view of a disposable set package in accordance with the invention.

Number 5 in FIG. 1 indicates as a whole a disposable set package for infusing a medicinal fluid, e.g. for dialysis treatment. The disposable set comprises an infusion device 6 having an outflow conduit 7, which is coiled about a protective support 8 and connected at one end to an infusion needle 9 carried by a finger-grip body 11. At the other end, conduit 7 is connected to a drip fitting 12, possibly fitted with a manually adjustable ring nut.

Figure 2:
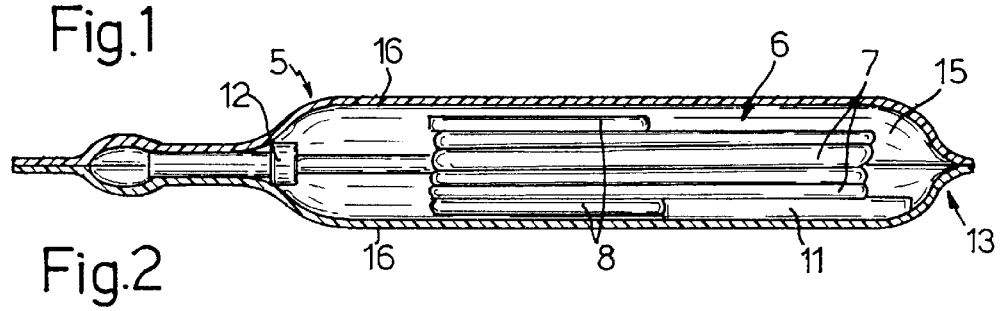
FIG. 2 shows a section along line II—II in FIG.

According to the invention, the package is defined by a single bag 13 made of flexible plastic material and comprising a first compartment 14 enclosing a given quantity of medicinal fluid for infusion, and a second compartment 15 enclosing infusion device 6. More specifically, bag 13 is defined by two substantially rectangular sheets 16 (FIG. 2) of transparent plastic material, e.g. PVC, having two short sides or outer edges 17 (FIG. 1), and two long sides or outer edges 18.

The two sheets 16 are heat sealed to each other along the four outer edges 17 and 18 to seal compartments 14 and 15 with respect to the outside environment, and also have another seal 19 dividing the package into two portions 20 and 21, of which, portion 20 forms compartment 14, and portion 21 incorporates compartment 15.

Seal 19 advantageously extends parallel to short edges 17 of the rectangle, so that portions 20 and 21 are both rectangular, and is so located that portion 20 forming fluid compartment 14 is larger than portion 21 incorporating compartment 15. Whatever the case, seal 19 separates compartments 14 and 15 in airtight manner.

Along edge 17, compartment 14 of bag 13 has an inlet fitting 22 through which the compartment is filled with a predetermined quantity of medicinal fluid for infusion; and fitting 22 is then closed in known manner by forming the usual break-off cone on the fitting and also applying a cap 23. At the top, bag 13 also comprises a portion 24 having a hole 25 by which to hook up the bag during infusion.

According to a further characteristic of the invention, a transparent-walled chamber 26 is provided between conduit 7 and compartment 14, and which is used as a drip to permit visual control of the infusion treatment. Chamber 26 is advantageously defined by a further seal 27 over a portion surrounding chamber 26 at a predetermined region.28 of bag 13, so that the walls of chamber 26 are defined by the two portions of sheets 16 of bag 13 at region 28.

Region 28 is advantageously defined by a rectangular portion of each sheet 16 located between seal 19 and two bottom-corner edges 17 and 18; and seal 27 extends over region 28 so that chamber 26 is ampoule-shaped.

Chamber 26 is connected to compartment 14 by a first fitting 29 made of rigid plastic material and defining a calibrated passage between compartment 14 and conduit 7, and is connected to conduit 7 by a bush 31 of drip fitting 12. Fitting 29 and bush 31 of fitting 12 are inserted into region 28 before seal 27 is formed.

The package described is formed as follows.

First of all, device 6 and fitting 29 are placed between two sheets 16, making sure drip fitting 12 is fully closed, and fitting 29 and bush 31 are so positioned at region 28 as to communicate with chamber 26 yet to be formed. Edges 17 and 18 are then sealed, seal 19 formed between portions 20 and 21, and seal 27 formed at region 28, all in one operation.

Compartment 14 is then filled with the medicinal fluid; fitting 22 is sealed with a break-off cone and fitted with cap 23; and package 5 is then sterilized, e.g. by immersing it for a predetermined time in an environment of suitable, appropriately controlled temperature and pressure.

Prior to use, part of compartment 15 is cut using scissors to free infusion device 6, so that infusion treatment can be commenced immediately.

The advantages, as compared with known sets, of the disposable set package according to the invention will be clear from the foregoing description. In particular, package 5 made of flexible, transparent material provides for eliminating a separate container for the fluid, while at the same time being compact.

Moreover, the component parts are assembled easily and cheaply; and drip chamber 26 enabling visual control of the infusion treatment is formed automatically with no fitting connection sealing problems.

Clearly, changes may be made to the package as described herein without, however, departing from the scope of the accompanying claims. For example, chamber 26 may be defined by a rigid plastic insert integral with fitting 29 and/or bush 31; and seal 19 separating portions 20 and 21 may be formed along an inclined, corner, or curved portion.

Moreover, region 28 may be located differently from as shown, and may be a different shape, e.g. oval; and one of the walls of compartment 15 may have an opening, closed with a strip of medicinal paper, through which to sterilize device 6 in known manner using ethylene gas.

What is claimed is:

1. A disposable set package for infusing a medicinal fluid into a patient's body, comprising an infusion device (6) having an outflow conduit (7) connected to a needle (9), said package (5) being defined by a single bag (13) comprising a first compartment (14) enclosing said fluid and a second compartment (15) enclosing said infusion device (6), said conduit communicating with said first compartment (14), said two compartments (14, 15) being comprised of two sheets (16) of flexible plastic material having outer edges (17, 18) sealed with respect to the outside environment, said compartments (14, 15) being separated from each other by another seal (19).

2. A package as claimed in claim 1, characterized in that said bag (13) is sterilized by immersion for a predetermined time in an environment of controlled temperature and pressure.

3. A package as claimed in claim 1, characterized in that a transparent chamber (26) acting as a drip is located between said conduit (7) and said first compartment (14).

4. A package as claimed in claim 3, characterized in that said chamber (26) is formed by a further seal (27) on a portion surrounding said chamber at a predetermined region (28) of said bag (13), a calibrated passage being located between said chamber (26) and said first compartment (14).

5. A package as claimed in claim 4, characterized in that said calibrated passage is defined by a fitting (29) inserted into said region (28), between said chamber (26) and said first compartment (14), prior to forming said other seal (19) and said further seal (27).

6. A package as claimed in claim 4, characterized in that said conduit (7) communicates with said chamber (26) by means of an adjustable drip fitting (12); a bush (31) of said drip fitting (12) being inserted into said region (28) prior to forming said further seal (27).

7. A package as claimed in claim 1, wherein said sheets (16) of plastic material are substantially rectangular and said other seal (19) extends parallel to the short edges (17) of the rectangle to divide said bag (13) into two portions (20, 21), one portion defining said first compartment (14) and the other incorporating said second compartment (15) and said chamber (26).

* * * * *